(12) United States Patent
Sasaki et al.

(10) Patent No.: US 7,499,170 B2
(45) Date of Patent: Mar. 3, 2009

(54) SYSTEM AND METHOD FOR READING A TEST STRIP

(75) Inventors: Hiroshi Sasaki, Fukuoka (JP); Michael Hutchinson, King of Prussia, PA (US)

(73) Assignee: FCC, LLC, West Palm Beach, FL (US)

( * ) Notice: Subject to any disclaimer, the term of this patent is extended or adjusted under 35 U.S.C. 154(b) by 250 days.

(21) Appl. No.: 11/485,402

(22) Filed: Jul. 12, 2006

(65) Prior Publication Data

US 2007/0013406 A1   Jan. 18, 2007

Related U.S. Application Data

(60) Provisional application No. 60/698,726, filed on Jul. 13, 2005.

(51) Int. Cl.
*G01N 21/00* (2006.01)

(52) U.S. Cl. .......................................... 356/436; 356/39

(58) Field of Classification Search .................... 356/39, 356/445–448, 73, 433, 436; 436/164–172; 422/58, 82.05, 82.09

See application file for complete search history.

(56) References Cited

U.S. PATENT DOCUMENTS

| | | | | |
|---|---|---|---|---|
| 5,889,585 | A | * | 3/1999 | Markart ........................ 356/39 |
| 6,055,060 | A | * | 4/2000 | Bolduan et al. ............. 356/433 |
| 6,707,554 | B1 | * | 3/2004 | Miltner et al. ............... 356/433 |
| 6,825,918 | B2 | * | 11/2004 | Eisenmann et al. ........... 356/39 |
| 7,317,532 | B2 | * | 1/2008 | Sharrock et al. ............ 356/436 |
| 2005/0036148 | A1 | | 2/2005 | Phelan |
| 2006/0051738 | A1 | * | 3/2006 | Zweig ........................... 435/4 |

FOREIGN PATENT DOCUMENTS

| EP | 0960946 | A2 | 1/1999 |
|---|---|---|---|
| EP | 1484611 | A2 | 8/2004 |

* cited by examiner

*Primary Examiner*—Hoa Q Pham
(74) *Attorney, Agent, or Firm*—Bernard L. Kleinke; Duckor Spradling Metzger & Wynne (57) ABSTRACT

A system and method is disclosed which relates to reading test strips. The method may include reading and storing initial values of a front photodiode and a rear photodiode, reading current values of the front and rear photodiodes, detecting at least one change between initial and current values in the front or the rear photodiodes, comparing the detected value change of one of the photodiodes with the value of the other photodiode, and determining a condition of the test strip in response to the resulting comparison.

26 Claims, 6 Drawing Sheets

SYSTEM AND METHOD FOR READING A TEST STRIP

RELATED APPLICATION

This application claims priority to U.S. provisional patent application, entitled SYSTEM AND METHOD FOR READING A TEST STRIP, Application No. 60/698,726, filed Jul. 13, 2005.

FIELD OF THE INVENTION

The present invention relates in general to a system and method of processing assay test results, and more particularly relates to a method of using it for assay tests such as a test of urine samples for pregnancy, drugs of abuse, tobacco, or other.

BACKGROUND ART

This section describes the background of the disclosed embodiment of the present invention. There is no intention, either express or implied, that the background art discussed in this section legally constitutes prior art.

Assay test strips have employed photo optic sensors to read color changes in liquid test samples. However, the background noise inherent with assay test strip designs may be a problem under certain circumstances when photo optically reading the result of a test strip. Background noise may, for example, be caused by additional dye that remains on the strip in the test area when the result is read. Background noise can sometimes cause the sensor to determine erroneously that the test line is present, when, in fact, it is not present.

The effects of a weakening battery for powering the photo optic sensor also may present a problem when reading the result of a test strip. Once the test kit is energized, the battery may slowly degrade over time. This may be difficult to monitor in certain circumstances. The low voltages may be erroneously interpreted as a wet strip or worse, a test line.

BRIEF DESCRIPTION OF THE DRAWINGS

The features of this invention and the manner of attaining them will become apparent, and the invention itself will be best understood by reference to the following description of certain embodiments of the invention taken in conjunction with the accompanying drawings, wherein.

CERTAIN EMBODIMENTS OF THE INVENTION

It will be readily understood that the components of the embodiments as generally described and illustrated in the drawings herein, could be arranged and designed in a wide variety of different configurations. Thus, the following more detailed description of the embodiments of the system, components and method of the present invention, as represented in the drawings, is not intended to limit the scope of the invention, as claimed, but is merely representative of certain embodiments of the invention.

According to certain embodiments of the invention, there is provided a method and system of electronically reading a test strip. The method includes reading and storing initial values of a front photodiode and a rear photodiode, reading current values of the front and rear photodiodes, detecting at least one change between initial and current values in the front or the rear photodiodes, comparing the detected value change of one of the photodiodes with the value of the other photodiode, and determining a condition of the test strip in response to the resulting comparison.

According to another embodiment of the invention, there is provided a method of electronically reading a test strip. The method includes providing a power source to an electronic reading circuit, reading and storing initial values of a front photodiode and a rear photodiode, continuing to read current values of the front and rear photodiode, calculating a result using the initial and current values of the front and rear photodiodes, starting a timer for a predetermined period of time when the result indicates adequate liquid has reached the rear photodiode; reading final values of the front and rear photodiodes at the end of the predetermined period of time, and calculating a final result using the final and initial values of the front and rear photodiodes.

Figure 1:
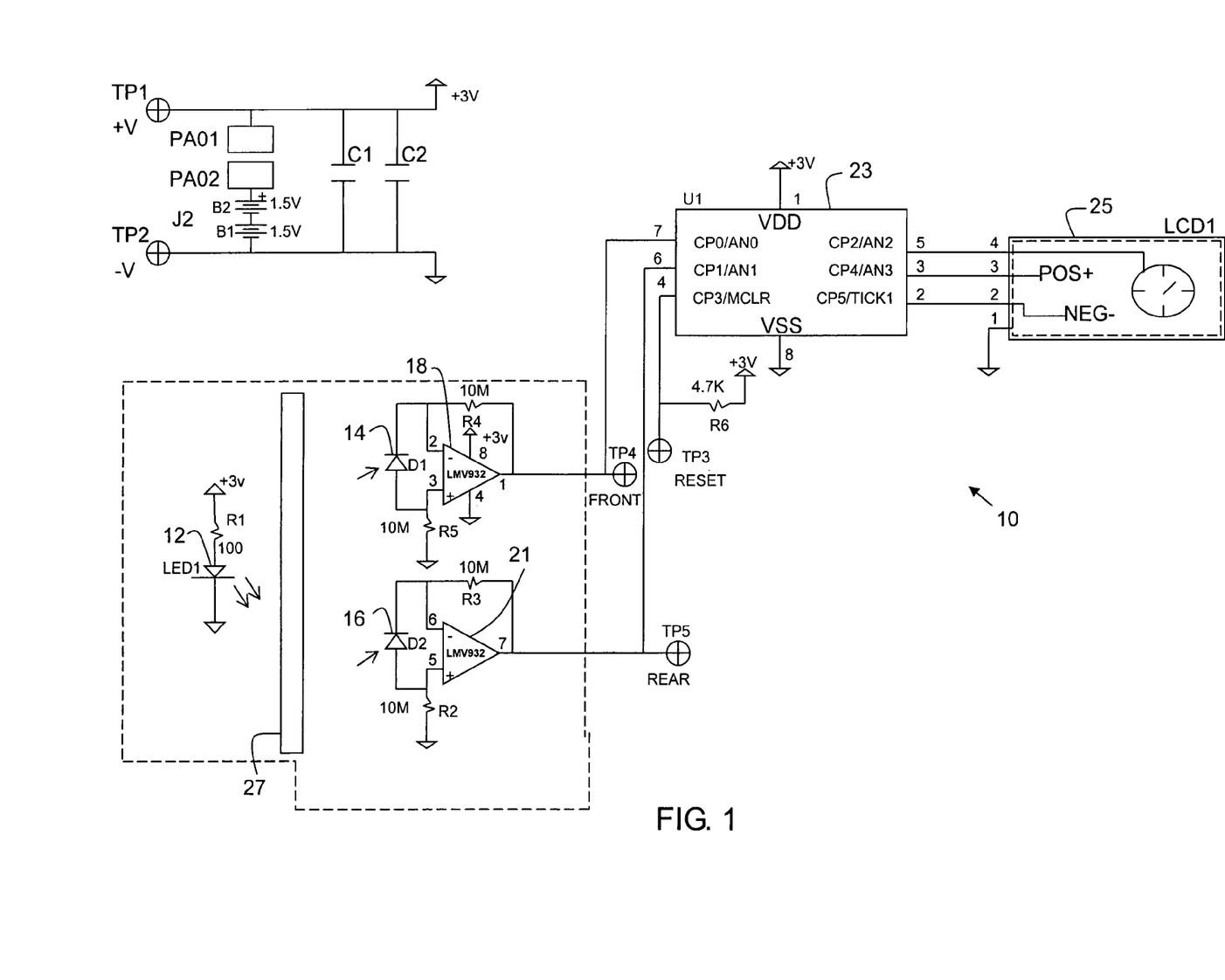
FIG. 1 is a schematic circuit diagram of an electronic reader.
Figure 2:
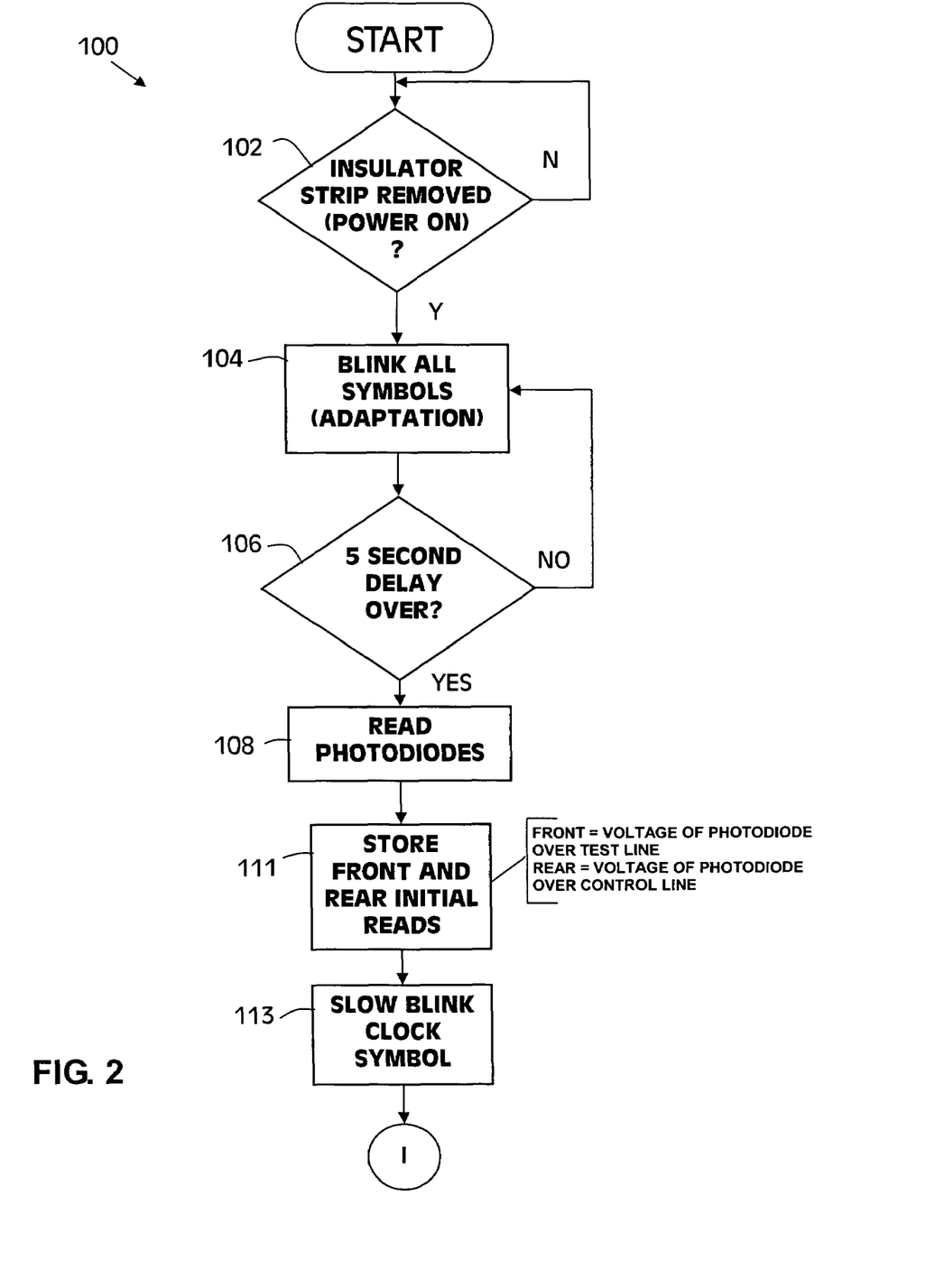
FIGS. 2 through 5 are flow chart diagrams of the software or firmware.
Figure 3:
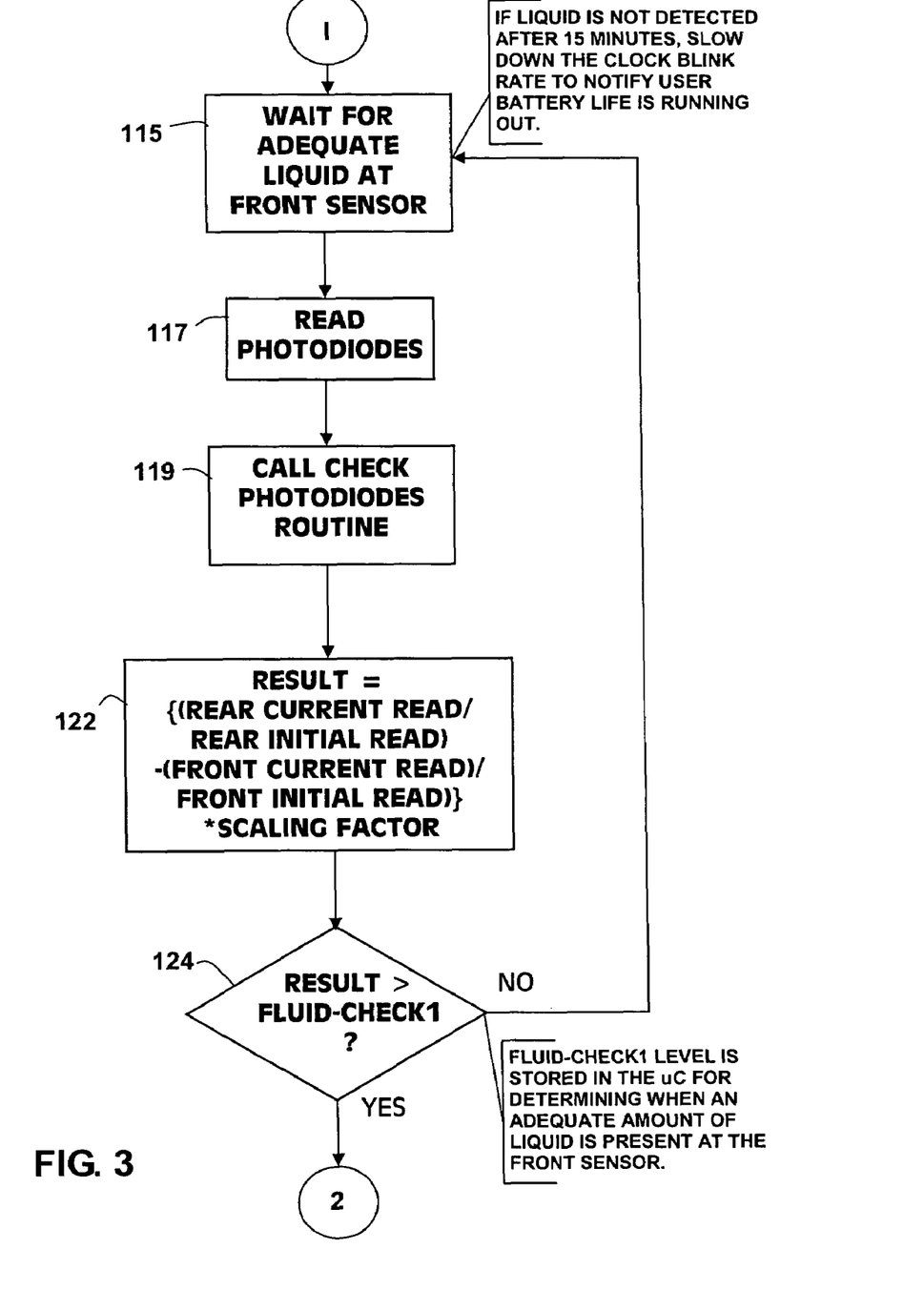
Figure 4:
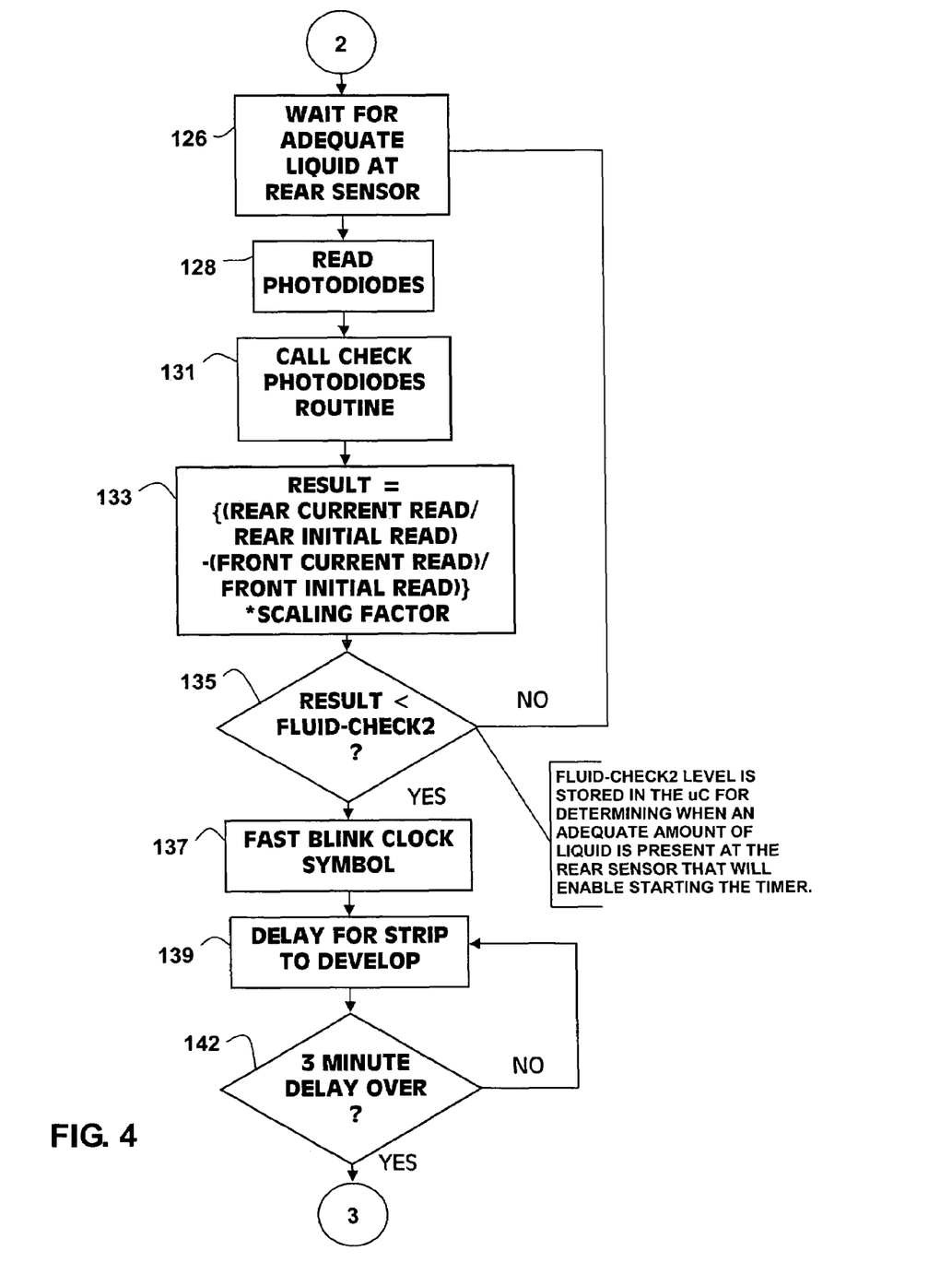
Figure 5:
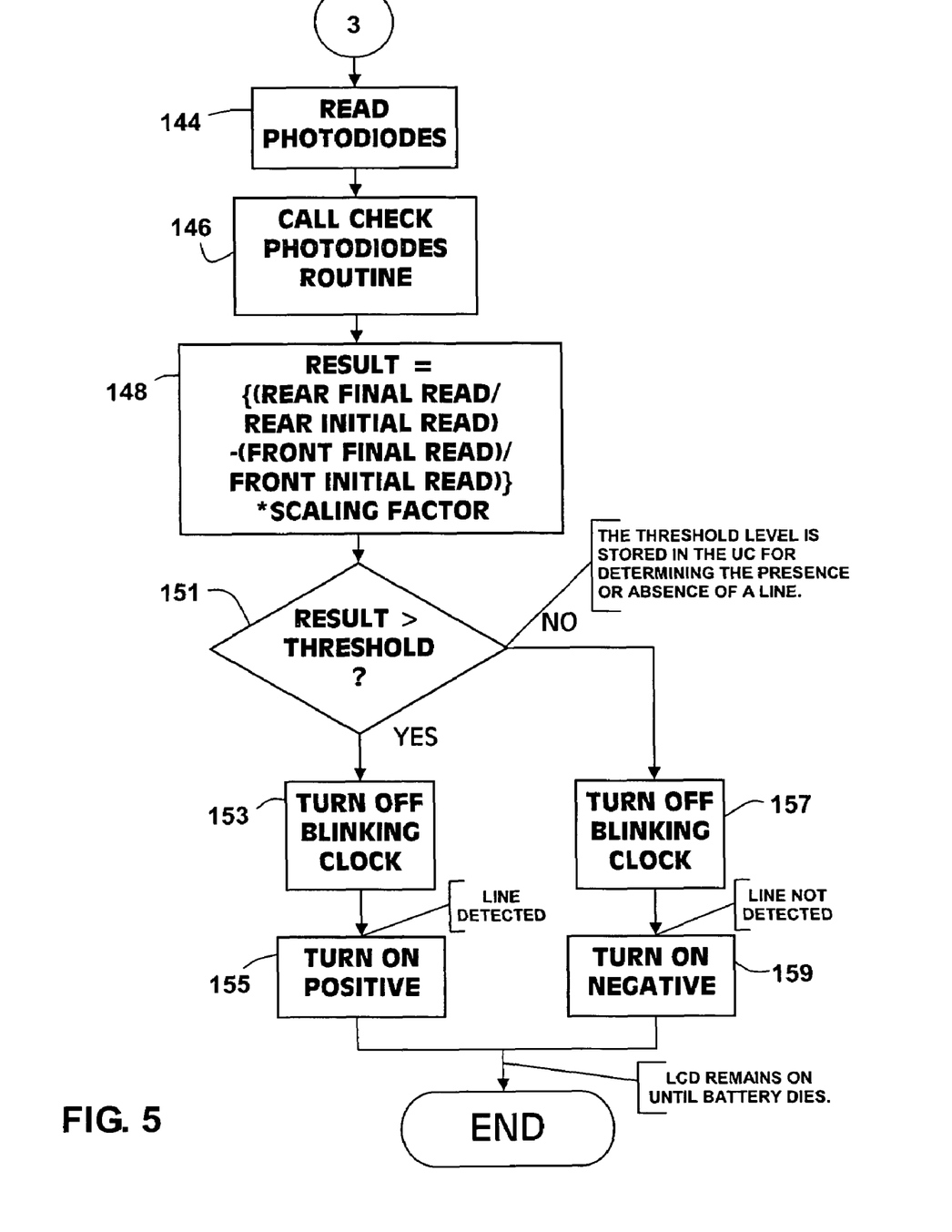

Referring now to FIG. 1 of the drawings, there is shown a schematic diagram of an electronic reader circuit 10 that may be used with embodiments of the present invention. The electronic reader circuit 10 may include an illuminator light emitting diode (LED) 12, a front photodiode 14, a rear photodiode 16, resistors R1-R5, a pair of operational amplifiers 18 and 21, a microcontroller 23, and a liquid crystal display (LCD) 25.

In operation the LED 12 illuminates a portion of a test strip 27 and the photodiodes 14 and 16 sense the intensity of the light at two sections of the test strip 27. A signal proportional to the intensity of the light may be generated using one of the photodiodes, a pair of the resistors, and one of the operational amplifiers for both the front and rear photodiodes. The signals may be provided to analog to digital inputs to the microcontroller 23. The microcontroller 23 may calculate the results using these signals and provide an input to the LCD 25 to display the result of the test.

The photodiodes 14 and 16 may assist in determining conditions of the test strip 27. Such conditions of the test strip 27 may include, but are not limited to, the following: 1) adequate fluid on the test strip 27 at the front photodiode 14, 2) adequate fluid on the test strip 27 at the rear photodiode 16, 3) no appearance of a line on the test strip 27 at the rear photodiode, and 4) appearance of a line on the test strip 27 at the rear photodiode. The appearance of a line on the test strip 27 may indicate the result of the test being accomplished on the test strip 27.

An electronic reader circuit having serially connected and oppositely oriented photodiodes, as described in PCT Patent Application No. PCT/US2006/026802, entitled TEST STRIP READER SYSTEM AND METHOD, filed on Jul. 7, 2006, and herein incorporated by reference, may also be utilized. This circuit may provide a timing pulse to the microcontroller representing the intensity of the light at the photodiodes.

Figure 6:
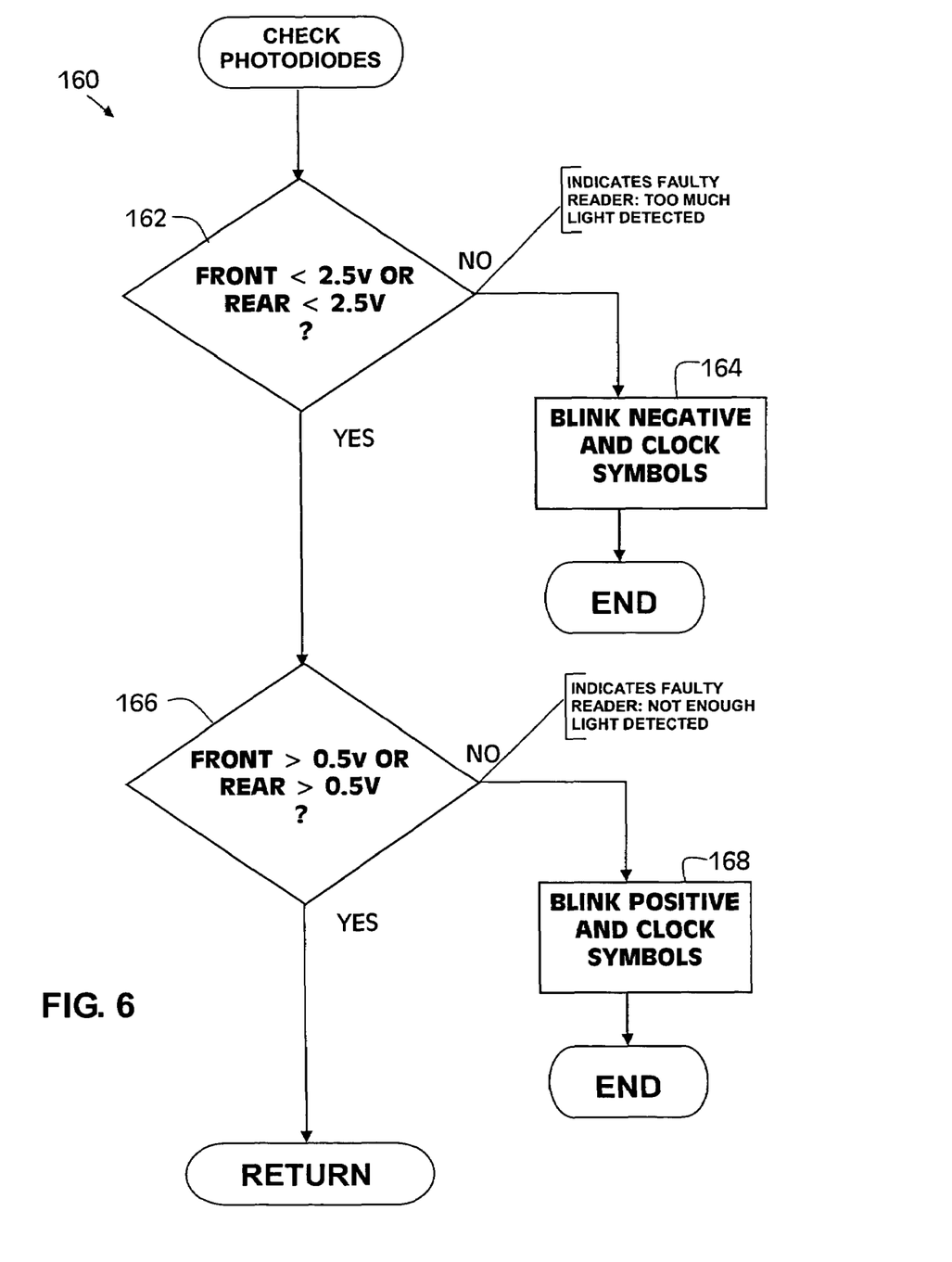
FIG. 6 is a flow chart diagram of a photodiode checker used by the software of FIGS. 2-5.

Referring now to FIGS. 2 through 6 of the drawings, a method of reading a test strip is shown. The main program, generally referenced as 100, is shown in FIGS. 2 through 5 and the check photodiodes routine, generally referenced as 160, is shown in FIG. 6. As indicated at the start, the system waits for the insulator strip to be removed and power provided to the system (step 102). Once power is provide, the microcontroller may blink the symbols on the LCD for approximately five seconds (steps 104 and 106). The photodiodes are then read and the initial readings for both the front and rear photodiodes are stored (steps 108 and 111). The microcontroller may then slowly blink the clock symbol on the LCD to indicate the system is ready for the application of the sample (step 113).

The microcontroller then waits for the application of adequate liquid at the front sensor (step 115). Both photodiodes are read (step 117) and the values checked to be valid in the check photodiode routine (step 119).

In the check photodiode routine 160 of FIG. 6, if the either value is greater than 2.5 volts (step 162) or less than 0.5 volts (166), the microcontroller may blink symbols on the LCD to indicate an invalid result (step 164 or 168, respectively) and end the test. A value greater than 2.5 volts may indicate a faulty reader that may be allowing too much light to be detected by the photodiode. A value less than 0.5 volts may also indicate a faulty reader such that not enough light is detected by the photodiode. If the values are less than 2.5 volts and greater than 0.5 volts, the microcontroller returns to the main program.

A check photodiode routine may also be adapted to utilize the timing pulse of the electronic reader circuit described in the above incorporated PCT application to check the health of the electronic reader circuit. Instead of comparing the photodiodes' values to a desired voltage range, the time periods of the timing pulse generated by the photodiodes may be compared to a desired time period range.

If the photodiode values are valid, a result is calculated (step 122) using the following equation:

$$\text{result} = [(R/R_i) - (F/F_i)] * SF \text{ where,}$$

$F_i$ = initial reading from front photodiode
F = current reading from front photodiode
$R_i$ = initial reading from rear photodiode
R = current reading from rear photodiode
SF = scaling factor The scaling factor is a large positive integer and is used to avoid values less than one in the calculations.

While the above equation may be preferred, other calculations may be utilized. The calculation may detect changes between the initial and current readings of the front and rear photodiodes and then compare these changes in the readings of the front and rear photodiodes. The calculation may also include, but is not limited to, finding the difference between the initial and current readings of the photodiodes and/or creating a ratio of the changes in the readings of the photodiodes.

In step 124, if the result from step 122 is less than the value of fluid-check1, the microcontroller continues to wait for adequate fluid at the front photodiode by repeating the above process. If the result is greater than the value of fluid-check1, the microcontroller moves on to wait for adequate fluid at the rear photodiode (step 126).

When waiting for adequate fluid at the rear photodiode, the microcontroller reads the values of the front and rear photodiodes (step 128). The values may be checked by the check photodiodes routine (step 131). If the values are valid, a result is calculated using the above equation (step 133). In step 135, if the result in step 133 is greater than the value of fluid-check2, the microcontroller continues to wait for adequate fluid at the rear photodiode by repeating the above process. If the result is less than the value of fluid-check2, the microcontroller may fast blink the clock symbol in the LCD (step 137) and may start a delay to allow the test strip to develop (steps 139 and 142).

At the end of the delay, three minutes for example, the microcontroller reads a final (last current) value for both the front and rear photodiodes (step 144). These final values may be checked to be valid by the check photodiodes routine (step 146). If the values are valid, a final result is calculated (step 148) using the following equation:

$$\text{final result} = [(R_f/R_i) - (F_f/F_i)] * SF \text{ where,}$$

$F_i$ = initial reading from front photodiode
$F_f$ = final reading from front photodiode
$R_i$ = initial reading from rear photodiode
$R_f$ = final reading from rear photodiode
SF = scaling factor The scaling factor may be the same value as used in the prior equation.

While the above equation may be preferred, other calculations may be utilized as described previously.

In step 151, if the final result in step 148 is greater than the threshold value, the microcontroller turns off the blinking clock symbol (step 153) and turns on the "POS +" symbol or other appropriate symbol (step 155). The appearance of a line opposite the rear photodiode may make this final result greater than the threshold value. If the final result is less than the threshold value, the microcontroller turns off the blinking clock symbol (step 157) and turns on the "NEG −" symbol or other appropriate symbol (step 159).

The embodiment described above takes advantage of the concept that the sensor output of the photodiode from a wet test strip may be much lower than the output from a dry strip. Since less light may be reflected off the test strip when it is wet, the output of the photodiode may be lower.

Both photodiodes in the above described embodiments may provide a proportional response and both photodiodes may track in a similar fashion, because both photodiodes may be exposed to the same environmental conditions and both photodiodes may be exposed to a similar light source.

To clarify what is meant by the phrases "proportional response" and "track in a similar fashion", assume both photodiodes are exposed to a light source of a particular wavelength and intensity. Also assume that the spacing between both photodiodes and the light source are similar. The light would cause each photodiode to produce an output response within its particular operating range. One output response could be greater than or less than the other output response. It doesn't matter! Now take the same two photodiodes and expose them to a light source with the same wavelength but with a lower intensity. The output response of each photodiode will be smaller than the previous output response, which means they track in a similar fashion.

If the ratio between the first and second readings for each photodiode is calculated, a comparison of these ratios may show them to be almost equivalent, which means the output responses of the photodiodes may be basically proportional. The proportional response may be a result of the very small intensity level change of the light source. The response curve of the photodiode may be considered linear over such a small intensity level change.

Using this proportionality of the output responses of the photodiodes, changes in the intensity of the light source may not invalidate the results of the test performed by the test strip reader. Thus a more reliable and efficient method and system of reading test strips may be achieved.

While particular embodiments of the present invention have been disclosed, it is to be understood that various different modifications and combinations are possible and are contemplated within the true spirit and scope of the disclosed embodiments. There is no intention, therefore, of limitations to the exact disclosure herein presented.

What is claimed is:

1. A method of electronically reading a test strip, comprising:
    illuminating two sections of the test strip using a light emitting diode;
    reading and storing initial values of a front photodiode and a rear photodiode, each photodiode receiving reflected light from a different one of the two sections;
    reading current values of the front and rear photodiodes;
    calculating a ratio of the current value to the initial value for each of the front and rear photodiodes;
    calculating a difference by subtracting the ratio of one of the photodiodes from the ratio of the other one of the photodiodes;
    comparing the difference to a predetermined threshold; and
    determining a condition of the test strip in response to the resulting comparison.

2. The method of claim 1, wherein determining the condition of the test strip includes determining whether adequate fluid has reached the front photodiode.

3. The method of claim 1, wherein determining the condition of the test strip includes determining whether adequate fluid has reached the rear photodiode.

4. The method of claim 3, further comprising:
    starting a timer for a predetermined period of time upon the determination that adequate fluid has reached the rear photodiode.

5. The method of claim 4, further comprising:
    reading final values of the front and rear photodiodes at the end of the predetermined period of time.

6. The method of claim 1, wherein determining the condition of the test strip includes determining whether a line has appeared at the rear photodiode.

7. The method of claim 1, wherein the comparing step includes calculating a result by multiplying the difference by a scale factor.

8. The method of claim 7, wherein determining the condition includes comparing the result to a threshold value.

9. The method of claim 1, further comprising:
    comparing the values of the front and rear photodiodes with a low threshold and a high threshold to determine validity of the values.

10. A system of electronically reading a test strip, comprising:
    means for illuminating a portion of the test strip using a light emitting diode, the portion including two spatially separated sections;
    means for reading and storing initial values of a front photodiode and a rear photodiode, each photodiode receiving reflected light from a different one of the two sections;
    means for reading current values of the front and rear photodiodes;
    means for calculating a ratio of the current value to the initial value for each of the front and rear photodiodes;
    means for calculating a difference by subtracting the ratio of one of the photodiodes from the ratio of the other one of the photodiodes;
    means for comparing the difference to a predetermined threshold; and
    means for determining a condition of the test strip in response to the resulting comparison.

11. The system of claim 10, wherein means for determining the condition of the test strip includes means for determining whether adequate fluid has reached the front photodiode.

12. The system of claim 10, wherein means for determining the condition of the test strip includes means for determining whether adequate fluid has reached the rear photodiode.

13. The system of claim 12, further comprising:
    means for starting a timer for a predetermined period of time upon the determination that adequate fluid has reached the rear photodiode.

14. The system of claim 13, further comprising:
    means for reading final values of the front and rear photodiodes at the end of the predetermined period of time.

15. The system of claim 10, wherein means for determining the condition of the test strip includes means for determining whether a line has appeared at the rear photodiode.

16. The system of claim 10, wherein means for comparing includes means for calculating a result by multiplying the difference by a scale factor.

17. The system of claim 16, wherein means for determining the condition includes means for comparing the result to a threshold value.

18. The system of claim 10, further comprising:
    means for comparing the values of the front and rear photodiodes with a low threshold and a high threshold to determine validity of the values.

19. A method of electronically reading a test strip, comprising:
    illuminating a portion of the test strip using a light emitting diode, the portion including two spatially separated sections;
    reading and storing initial values of a front photodiode and a rear photodiode, each photodiode receiving reflected light from a different one of the two sections;
    reading current values of the front and rear photodiodes;
    calculating ratios of the initial and current values of the front and rear photodiodes;
    starting a timer for a predetermined period of time when the result indicates adequate fluid has reached the rear photodiode;
    reading final values of the front and rear photodiodes at the end of the predetermined period of time;
    calculating a difference by subtracting the ratio of one of the photodiodes from the ratio of the other one of the photodiodes;
    comparing the difference to a predetermined threshold; and
    calculating a final result using the final and initial values of the front and rear photodiodes and in response to the resulting comparison.

20. The method of claim 19, further comprising:
    providing a power source to an electronic reading circuit.

21. The method of claim 20, further comprising:
    delaying for a predetermined delay time subsequent providing the power source and prior to reading the initial values.

22. The method of claim 19, further comprising:
    comparing the result to a threshold to determine whether adequate fluid has reached the front photodiode.

23. The method of claim 19, further comprising:
    comparing the result to a threshold to determine whether adequate fluid has reached the rear photodiode.

24. The method of claim 19, further comprising:
comparing the final result to a threshold to determine a test result of the test strip.

25. The method of claim 19, wherein the result is calculated using the following equation:

$$\text{result} = [(\text{rear photodiode current value}/\text{rear photodiode initial value}) - (\text{front photodiode current value}/\text{front photodiode initial value})] * \text{scaling factor}.$$

26. The method of claim 19, wherein the final result is calculated using the following equation:

$$\text{final result} = [(\text{rear photodiode final value}/\text{rear photodiode initial value}) - (\text{front photodiode final value}/\text{front photodiode initial value})] * \text{scaling factor}.$$

* * * * *